(12) United States Patent
Anselmi et al.

(10) Patent No.: US 7,211,632 B2
(45) Date of Patent: May 1, 2007

(54) PERDEUTERATED POLYIMIDES, THEIR PROCESS OF PREPARATION AND THEIR USE AS MATERIALS WHICH ARE TRANSPARENT WITHIN THE REGION FROM 2500 TO 3500CM$^{-1}$

(75) Inventors: Elsa Anselmi, Garches (FR); Jacques Raby, Grenoble (FR); Alexia Balland-Longeau, Tours (FR); Marc Calonne, Drache (FR)

(73) Assignee: Commissariat a L'Energie Atomique, Paris (FR)

( * ) Notice: Subject to any disclaimer, the term of this patent is extended or adjusted under 35 U.S.C. 154(b) by 54 days.

(21) Appl. No.: 10/527,630

(22) PCT Filed: Apr. 6, 2004

(86) PCT No.: PCT/FR2004/050145

§ 371 (c)(1),
(2), (4) Date: Mar. 14, 2005

(87) PCT Pub. No.: WO2004/092249

PCT Pub. Date: Oct. 28, 2004

(65) Prior Publication Data

US 2005/0239973 A1    Oct. 27, 2005

(30) Foreign Application Priority Data

Apr. 8, 2003    (FR) .................... 03 50090

(51) Int. Cl.
*C08G 73/12* (2006.01)
*C07D 209/48* (2006.01)

(52) U.S. Cl. ............... 525/420.5; 548/467; 548/473
(58) Field of Classification Search ............ 525/420.5; 548/467, 473
See application file for complete search history.

(56) References Cited

U.S. PATENT DOCUMENTS

| | | | |
|---|---|---|---|
| 5,233,018 | A | 8/1993 | Ando et al. |
| 6,048,968 | A | 4/2000 | Etzbach et al. |
| 6,048,986 | A | 4/2000 | Ando et al. |

OTHER PUBLICATIONS

Kaino, Toshikuni "Polymers for Optical Transmission and Optical Signal Processing" Reports on Progress in Polymer Physics in Japan 2000, vol. 43, pp. 433-466.*

Artamkina, G. A., et al., "Oxidation of Alkyl Aromatic Compounds with Potassium Permanganate Under the Conditions of Interphase Catalysis", *Translated from Zhurnal Organicheskoi Khimii*, Apr. 1980, pp. 698-702, vol. 16, No. 4, Translation.

Kaino, Toshikuni, "Polymers for Optical Transmission and Optical Signal Processing", *Reports on Progress in Polymer Physics in Japan*, 2000, pp. 433-466, vol. 43.

St. Clair, Anne K., et al., "Evaluation of Colorless Polyimide Film Thermal Control Coating Applications", *SAMPE Journal*, Jul./Aug. 1985, pp. 28-33.

Wallace, W. E., et al., "Gas Absorption During Ion-Irradiation of a Ployer Target", *Nuclear Instruments and Methods in Physics Research*, 1995, pp. 435-439, B103, Search Report.

Werstiuk, Nick H., et al., "The High Temperature and Dilute Acid (HTDA) Procedure as a General Method of Replacing Aromatic Hydrogen by Deuterium. II$^{1-3}$", *Canadian Journal of Chemistry*, 1973, pp. 2169-2171, vol. 52.

Kaino, Toshikuni, "Polymers for Optical Transmission and Optical Signal Processing", *Reports on Progress in Polymer Physics in Japan*, 2000, pp. 433-466, vol. 43.

* cited by examiner

*Primary Examiner*—Kamal A. Saeed
*Assistant Examiner*—Joseph R. Kosack
(74) *Attorney, Agent, or Firm*—Hutchison Law Group PLLC

(57) ABSTRACT

The present invention relates to a deuterated polyimide, the backbone of which comprises an alternation between:
at least one repeat unit corresponding to the following formula (I):

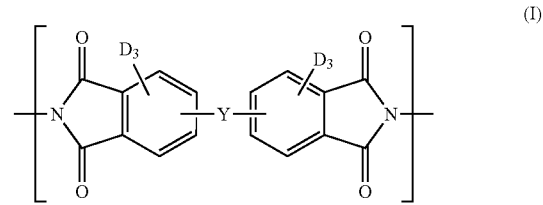

in which:
Y represents a single bond or a spacer group; and
at least one repeat unit corresponding to the following formula (II):

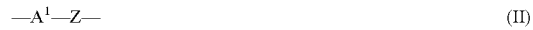

in which:
$A^1$ represents a perdeuterated aromatic group comprising from 6 to 10 carbon atoms;
Z represents a single bond or a group chosen from —O—$C_6D_4$—, —CO—$C_6D_4$— and —$C_6D_4$—.

These polyimides are used in particular as materials which are transparent within the region from 2500 to 3500 cm$^{-1}$, for example in laser devices.

12 Claims, No Drawings

PERDEUTERATED POLYIMIDES, THEIR PROCESS OF PREPARATION AND THEIR USE AS MATERIALS WHICH ARE TRANSPARENT WITHIN THE REGION FROM 2500 TO 3500CM$^{-1}$

This application is a 35 U.S.C. 371 filing of PCT/FR04/50145 filed Apr. 6, 2004.

TECHNICAL FIELD

The invention relates to deuterated aromatic polyimides exhibiting at the same time excellent mechanical, thermal and optical properties and exhibiting a transparency within the region from 2500 to 3500 cm$^{-1}$ of the infrared spectrum and to a process for the preparation of these polymers and the use of these polymers in the form of films.

These polyimides are applied in particular, due to their excellent mechanical, thermal and optical properties, in the preparation of organic materials for high-power lasers used in particular when nuclear physics experiments are carried out.

The general field of the invention is therefore that of organic materials exhibiting a transparency within a given wavelength range.

It is specified that, in the context of this description, the term "materials which are transparent within a given wavelength range" is understood to mean materials capable of allowing the passage, without absorption, of optical signals with wavelength(s) belonging to the abovementioned range.

Generally, organic materials, such as organic polymers, can result in a degree of optical attenuation of optical signals passing through them, that is to say a loss in intensity of these light signals. This optical attenuation observed with organic polymers can be attributed to the absorption of certain wavelengths by the constituent bonds of the polymer (such as the absorption of the harmonics of the valence vibrational bands of the C—H bonds) and also to scattering. This optical attenuation is thus related directly to the chemical structure of the polymer.

STATE OF THE ART

Many studies have thus focused on the search for organic polymers exhibiting a chemical structure capable of reducing optical losses related to absorption.

Thus, the author Kaino, in the paper 'Polymers for Optical Transmission and Optical Signal Processing', Reports on Progress in Polymer Physics in Japan, vol. 43, 2000 [1], describes deuterated and/or fluorinated polymers, such as polymethyl methacrylate (PMMA) and polystyrene (PS), exhibiting a reduced optical attenuation in comparison with their non-deuterated and/or nonfluorinated analogs. However, these polymers exhibit the disadvantage of not being very stable thermally, insofar as they cannot be used for temperatures ranging above 80° C. These polymers thus cannot be used in fields, such as optoelectronics and high-power lasers, which require much better thermal properties than those of these polymers.

Aromatic polyimides are polymers capable of exhibiting better mechanical and thermal properties. However, these polymers, due to the presence of a large number of C—H bonds, exhibit very high optical losses. In order to counter this disadvantage, numerous authors have sought to modify the structure of these polyimides, in particular by modifying the C—H bonds, so as to obtain polyimides exhibiting the lowest possible optical losses, in particular in the infrared region.

The author of the document [1] and the authors Saint-Clair et al., in the paper <<Evaluation of Colorless Polyimide Film for Thermal Control Coating Applications >>, Sampe Journal, August 1985, pp. 28–33 [2], have described an aromatic polyimide comprising a unit:

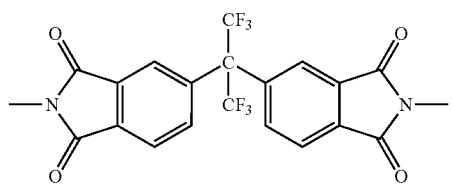

Due to the presence of a hexafluoroiso-propylidene group, these polyimides exhibit a weaker absorption in the infrared than the hydrogen-comprising analogs and thus a lower optical loss in this region. However, these polymers still comprise C—H bonds in the phenyl group and thus a significant absorption within the region from 2500 to 3500 cm$^{-1}$ of the infrared spectrum. This rules out these polyimides from being used in an application in the field of high-power lasers.

The authors Ando et al., in United States patents U.S. Pat. No. 5,233,018 [3] and U.S. Pat. No. 6,048,986 [4], disclose polyimides perfluorinated so as to obtain a reduction in the absorption peaks in an optical transmission window situated in the near infrared, that is to say from 5880 to 10 000 cm$^{-1}$. However, these polymers are not completely transparent within the region lying between 2500 and 3500 cm$^{-1}$, namely a transmission region employed in high-power lasers.

Finally, the authors Wallace et al., in the paper 'Gas Absorption during ion-irradiation of a polymer target', Nuclear Instruments and Methods in Physics Research B 103 (1995), 435–439 [5], have described a partially deuterated (to 23%) polyimide comprising a pyromellitic dianhydride/oxydianiline unit. However, this polymer exhibits mechanical properties, such as a tensile strength of approximately 110 MPa, and optical properties which are inadequate for application in the field of high-power lasers.

Thus, the polymers of the prior art all exhibit one or more of the following disadvantages:

they exhibit inadequate thermal properties;
they exhibit absorption peaks with an excessively high intensity (that is to say, an excessively high optical attenuation) within a given transmission window, in particular within the transmission window between 2500 cm$^{-1}$ and 3500 cm$^{-1}$
they exhibit mechanical properties compatible with difficulty with the use of these polymers in fields requiring very good mechanical properties.

ACCOUNT OF THE INVENTION

One aim of the present invention is to provide novel polymers which do not exhibit the abovementioned disadvantages of the polymers of the prior art and which exhibit in particular good mechanical performances (such as a tensile strength of greater than 110 MPa) and complete transparency within a transmission region from 2500 to 3500 cm$^{-1}$.

One aim of the present invention is also to provide a process for the preparation of polymers in accordance with the present invention.

Another aim of the present invention is to provide monomers which can be used in the context of the process of the invention.

One aim of the present invention is also to provide processes for the preparation of such monomers.

Finally, one aim of the present invention is to provide films based on polymers in accordance with the invention.

The present invention relates, according to a first subject matter, to a deuterated polyimide, the backbone of which comprises an alternation between:

at least one repeat unit corresponding to the following formula (I):

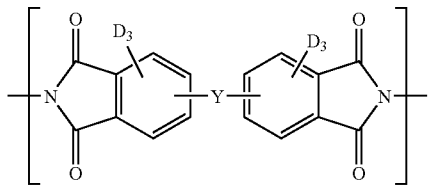

in which:
Y represents a single bond or a spacer group; and
at least one repeat unit corresponding to the following formula (II):

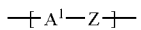

in which:
$A^1$ represents a perdeuterated aromatic group comprising from 6 to 10 carbon atoms;
Z represents a single bond or a group chosen from —O—$C_6D_4$—, —CO—$C_6D_4$— and —$C_6D_4$—.

Thus, the polyimides of the invention correspond to alternating polymers, the backbone of which comprises an alternation between at least one unit of formula (I) and at least one unit of formula (II). In other words, said units are linked together in the following way:

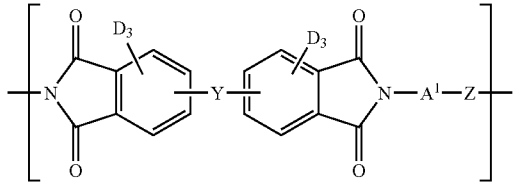

In addition to the alternation between at least one unit of formula (I) and at least one unit of formula (II), the backbone of the polyimides of the invention can comprise other units, such as a unit of formula (III), as explained below.

When the polyimides of the invention comprise different repeat units of formula (I) and different repeat units of formula (II), the alternation in the backbone between the different units of formula (I) and the different units of formula (II) will be random.

According to the invention, the term "single bond" is understood to mean a covalent bond. Thus, when Z represents a single bond, the unit of formula (II) corresponds to a unit of formula —$A^1$—.

It is specified that the term "spacer group" is understood to mean a group which forms a bridge between the two phenyl groups and which is bonded to the latter via covalent bonds.

It is specified that $D_3$ means that the phenyl rings are substituted by 3 deuterium atoms.

Surprisingly, the authors of this invention were able to determine that these polyimides exhibit excellent mechanical properties, such as a tensile strength $\sigma_b$ of greater than 110 MPa, a Young's modulus E of greater than 2 GPa and an elongation at break $\epsilon_b$ of greater than or equal to 10%.

Furthermore, the polyimides of the invention are capable of withstanding temperatures of between −253 and 400° C., which renders these polyimides applicable within a very wide range of temperatures.

Finally, the fact that these polyimides comprise perdeuterated aromatic groups contributes to rendering these polymers transparent within the infrared region between 2500 and 3500 cm$^{-1}$.

As mentioned above, the polyimides of the invention correspond to perdeuterated aromatic polyimides, that is to say all the hydrogen atoms of which carried by the aromatic groups are replaced by deuterium atoms.

It is specified that the term "perdeuterated aromatic group" is understood to mean, previously and subsequently, a perdeuterated benzene group or a perdeuterated naphthalene group.

The group Y forming a bridge between these phenyl groups can be a single bond or a spacer group. When Y is a spacer group, it can be chosen from —O—, —$CD_2$—, —CO—, —$SO_2$— or —$C_6D_4$—.

Preferably, the repeat number of the units of formula (I) is equal to the repeat number of the units of formula (II).

Specific polyimides in accordance with the present invention are polyimides, the backbone of which comprises an alternation between a repeat unit of formula (I) defined above and a repeat unit of formula (IIa):

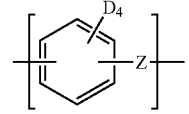

in which Z corresponds to the same definition as that given above.

Even more specific polyimides are the polyimides chosen from:

polyimides comprising a repeat unit of following formula (Ia) and a repeat unit of following formula (IIb):

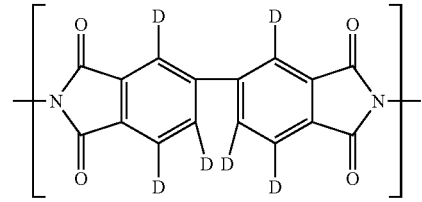

(IIb)

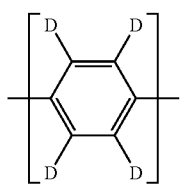

polyimides comprising a repeat unit of following formula (Ia) and a repeat unit of following formula (IIc):

(Ia)

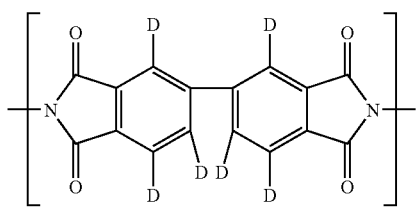

(IIc)

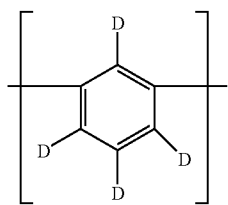

polyimides comprising a repeat unit of following formula (Ia) and a repeat unit of following formula (IId):

(Ia)

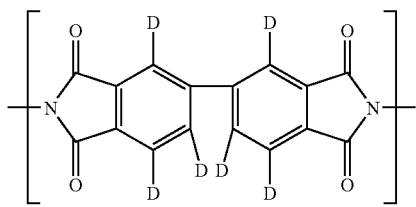

(IId)

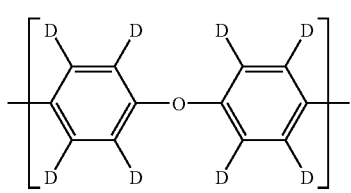

polyimides comprising a repeat unit of following formula (Ib) and a repeat unit of following formula (IIb):

(Ib)

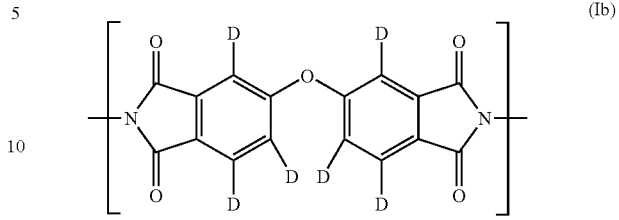

(IIb)

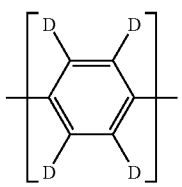

polyimides comprising a repeat unit of following formula (Ib) and a repeat unit of following formula (IId):

(Ib)

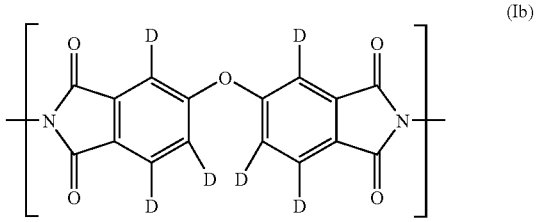

(IId)

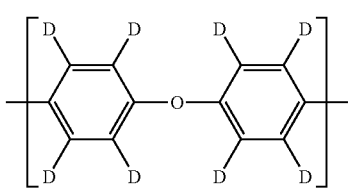

polyimides comprising a repeat unit of following formula (Ic) and a repeat unit of following formula (IIb):

(Ic)

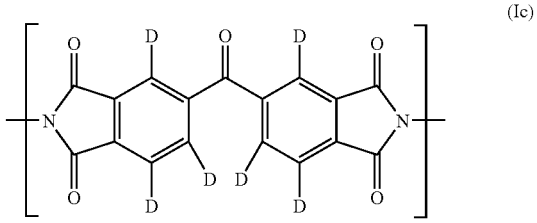

(IIb)

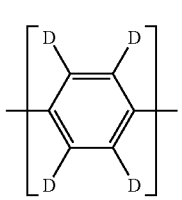

polyimides comprising a repeat unit of following formula (Ic) and a repeat unit of following formula (IId):

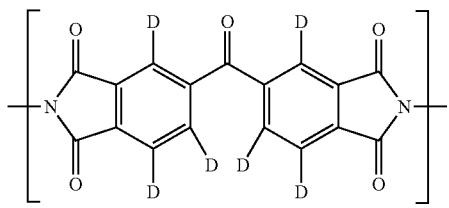
(Ic)

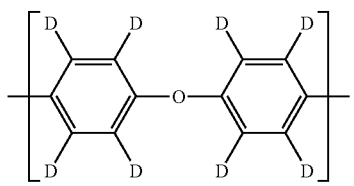
(IId)

polyimides comprising a repeat unit of following formula (Id) and a repeat unit of following formula (IId):

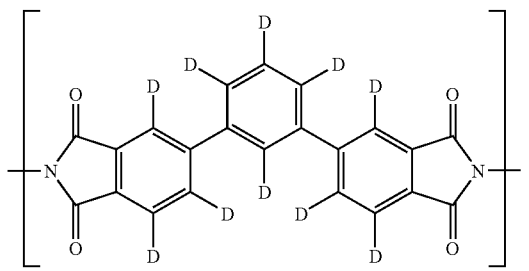
(Id)

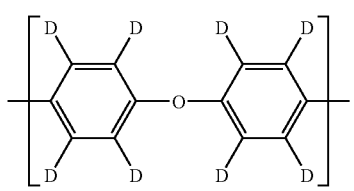
(IId)

polyimides comprising a repeat unit of following formula (Ia), a repeat unit of following formula (IIb) and a repeat unit of following formula (IId):

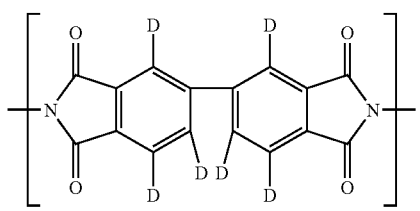
(Ia)

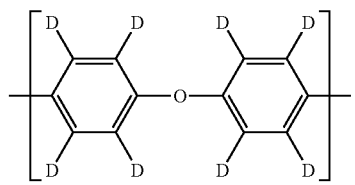
(IId)

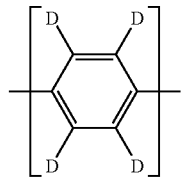
(IIb)

polyimides comprising a repeat unit of following formula (Ic), a repeat unit of following formula (IIb) and a repeat unit of following formula (IId):

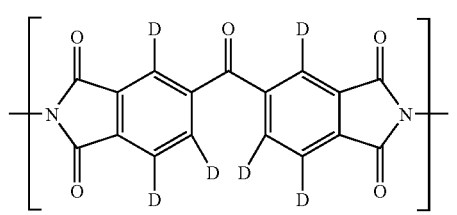
(Ic)

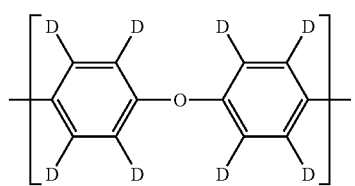
(IId)

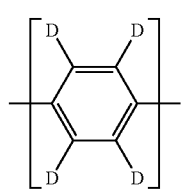
(IIb)

It is understood that, according to the invention, these specific polyimides comprise a backbone composed of an alternation between a specific unit coming within the definition of the units of formula (I) and a specific unit coming within the definition of the units of formula (II).

These specific polymers exhibit in particular complete transparency within the region extending from 2500 to 3500 cm$^{-1}$ and excellent mechanical properties, such as a tensile strength of greater than 110 MPa.

According to the invention, the deuterated polyimides can additionally comprise other imide units, in particular an imide unit corresponding to the following formula (III):

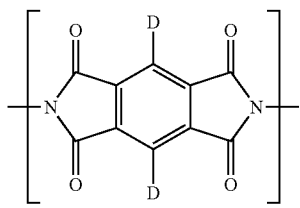

In this scenario, the polyimides will comprise a backbone formed of an alternation between a unit of formula (I) and a unit of formula (II) and of an alternation between a unit of formula (II) and the unit of formula (III).

In other words, the backbone will comprise the following units:

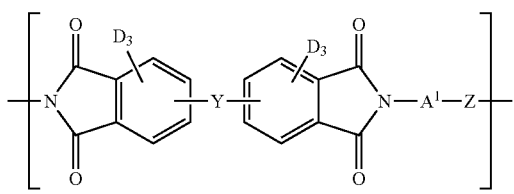

and:

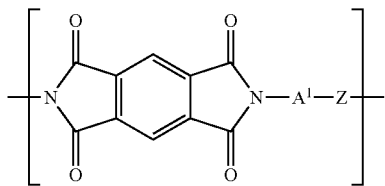

the order in which the units are linked together being random.

Specific polyimides corresponding to the definition given in the preceding paragraph are polyimides comprising a repeat unit of following formula (Ia), a repeat unit of following formula (IIb) and a repeat unit of following formula (III):

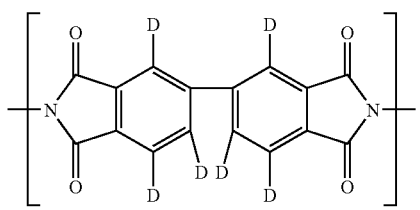

-continued

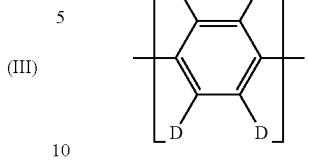

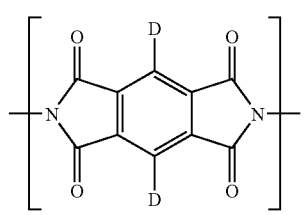

In this case, the alternation in the backbone will take place between the unit of formula (Ia) and the unit of formula (IIb) and between the unit of formula (III) and the unit of formula (IIb), this alternation occurring randomly.

The polyimides in accordance with the present invention can be prepared by any type of process.

In particular, the polyimides of the invention can be prepared by a process comprising a stage consisting in treating, by heating at an appropriate temperature, a solution of a poly(amide-acid), the backbone of which comprises an alternation between at least one repeat unit of formula (IV):

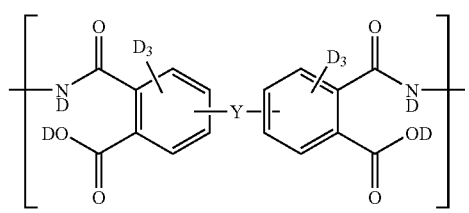

in which Y corresponds to the same definition as that given above; and at least one repeat unit of formula (II):

in which $A^1$ and Z correspond to the same definitions as those given above, the appropriate heating temperature being determined so as to obtain complete imidization of said poly(amide-acid).

When the polyimides of the invention also comprise a unit of formula (III) as defined above, these polyimides are prepared from a solution of poly(amide-acid), the backbone of which simultaneously comprises:

an alternation between at least one repeat unit of formula (IV) and a unit of formula (II), which amounts to saying that the poly(amide-acid) comprises a repeat unit of formula:

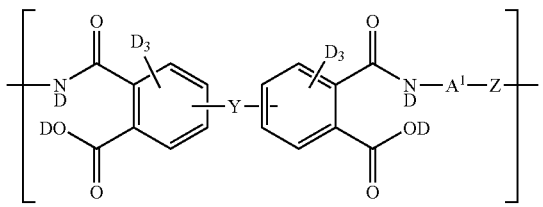

and
an alternation between a unit of formula (IVa):

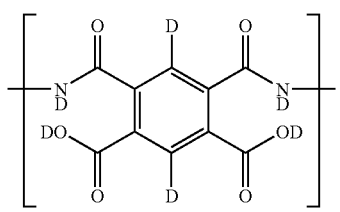

and at least one unit of formula (II), which amounts to saying that the poly(amide-acid) comprises a repeat unit of following formula:

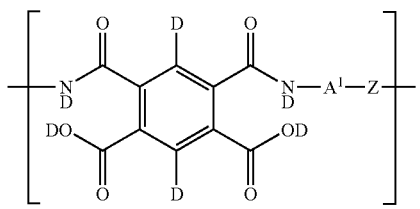

The heating at an appropriate temperature can be carried out in air or preferably under an inert gas atmosphere, such as an argon or nitrogen atmosphere, at a temperature ranging, for example, from 80 to 400° C., for a time ranging, for example, from 1 to 8 hours.

According to the process of the invention, the abovementioned poly(amide-acid) solution can be prepared by polycondensation, in a solvent, of at least one monomer of following formula (V):

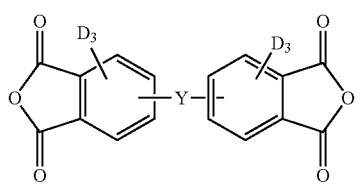
(V)

in which Y corresponds to the same definition as that given above, and
of at least one monomer of following formula (VI):

$ND_2-A^1-Z-ND_2$ (VI)

in which $A^1$ and Z correspond to the same definitions as those given above, the monomers of formulae (V) and (VI) preferably being reacted in stoichiometric proportions.

When the poly(amide-acid) solution also comprises a unit of formula (IVa), the polycondensation will also be carried out in the presence of a monomer of following formula:

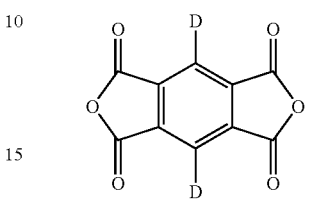

The preparation of this poly(amide-acid) solution is preferably carried out in a dipolar aprotic solvent, such as N-methylpyrrolidone (NMP), dimethylformamide (DMF) and dimethylacetamide (DMAC), at ambient temperature under an inert gas atmosphere, it being possible for the concentration of the solution to vary, for example, from 5 to 15%.

In order to obtain a poly(amide-acid) precursor of high molecular mass, the abovementioned monomers should preferably be brought together in stoichiometric proportions. Furthermore, the monomers will advantageously be purified before use in order to remove any trace of water, which might bring about the hydrolysis of the dianhydride monomer, and any trace of impurities which might unbalance the stoichiometry. These monomers can be purified, for example, by sublimation.

Another subject matter of the invention is dianhydride monomers which can be used in the context of the process of the invention, corresponding to the following formula (V):

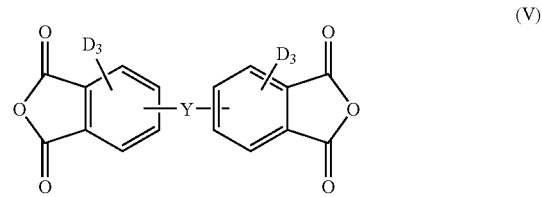
(V)

in which Y corresponds to the same definition as that given above.

Specific monomers in accordance with the formula (V) are monomers with the following formulae:

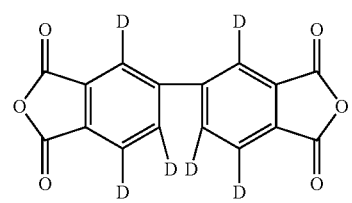

-continued

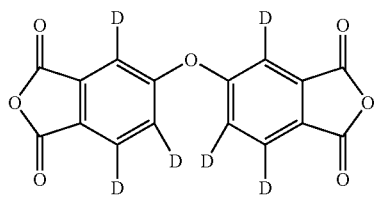

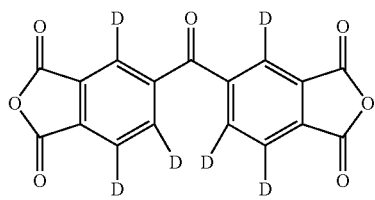

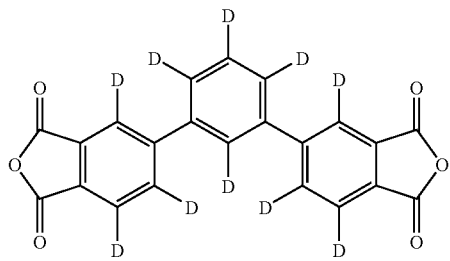

The deuterated diamine monomers which can be used in the context of the process of the invention are monomers corresponding to the following general formula (VI):

in which $A^1$ and Z correspond to the same definitions as those given above.

Specific diamine monomers in accordance with the formula (VI) are the monomers with the following formulae:

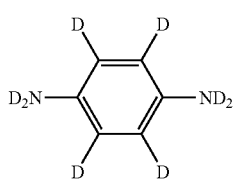    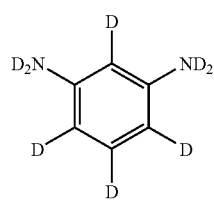

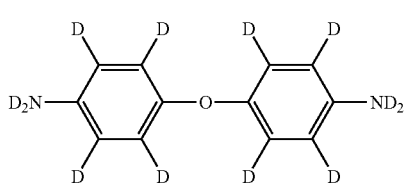

These deuterated diamine monomers are available in particular from Aldrich and CDN-Isotopes.

Another subject matter of the invention is a process for the preparation of monomers of following formula (V):

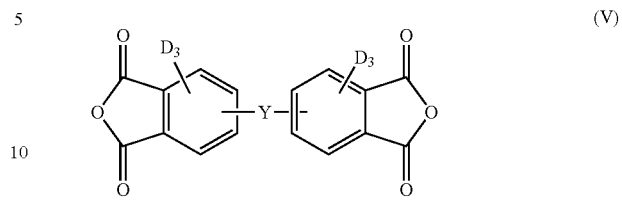

in which Y corresponds to the same definition as that given above, said process successively comprising the following stages:

subjecting a compound of following formula (VII):

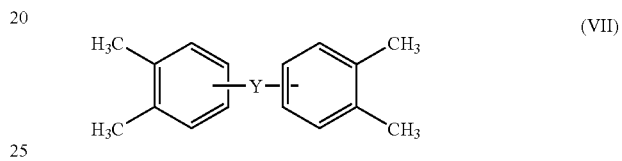

to deuteration, so as to obtain a compound of following formula (VIII):

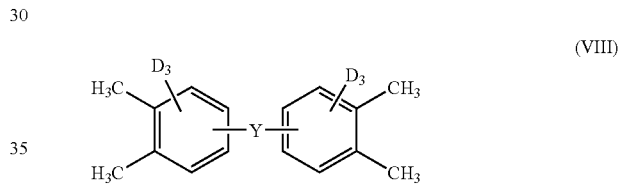

subjecting the compound obtained above to oxidation, so as to obtain a compound of following formula (IX):

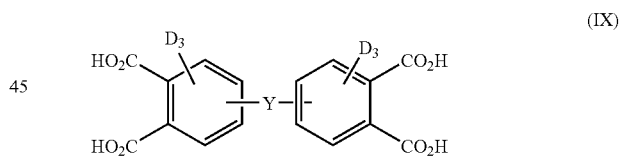

subjecting the compound obtained above to cyclodehydration, so as to obtain the compound of formula (V).

The starting tetramethyl compounds represented by the formula (VII) are compounds available commercially from Lancaster or can be prepared, if appropriate, by methods of synthesis within the scope of a person skilled in the art. These starting compounds in accordance with the process of the invention are subjected to a stage of complete deuteration of the aromatic rings without deuteration of the methyl groups, so as to obtain the compounds represented by the formula (VIII). This deuteration stage is advantageously carried out by heating the starting tetramethyl compound in a deuterated acidic medium (such as a DCl solution) and in the presence of deuterated water at an appropriate temperature, for example 250° C., under a moderate pressure, that is to say a pressure which can range up to 40–45 bar. This deuteration stage is advantageously carried out in a Parr apparatus, which is an apparatus intended for reactions to be carried out under moderate pressure. The deuteration stage explained above is described in more detail in the publication by Werstiuk et al. <<The High Temperature and Dilute Acid (HTDA) Procedure as a General Method of Replacing Aromatic Hydrogen by Deuterium >>, Can. J. Chem., vol. 52, 2169–2171, 1973 [6].

The deuterated compounds of formula (VIII) are subsequently subjected to an oxidation stage intended to convert the methyl groups to —COOH groups. This oxidation stage is advantageously carried out by reacting the compound of formula (VIII) with potassium permanganate in a two-phase medium (aqueous phase/organic phase) in the presence of a phase transfer agent. The organic phase can be composed, for example, of a halogenated solvent, such as dichloroethane, and the phase transfer agent can be an ammonium salt, such as tetrabutylammonium bromide or cetyltrimethylammonium bromide. Further teachings regarding this oxidation stage, and in particular the reaction mechanism involved, appear in the publication by Artamkina et al. in <<Oxidation of Alkyl Aromatic Compounds With Potassium Permanganate Under The Conditions of Interphase Catalysis >>, translated from Zhurnal Organicheskoi Khimii, vol. 16, No. 4, 99, 698–702, April 1980 [7].

Finally, the tetracarboxyl compound of formula (IX) is subjected to a cyclodehydration stage. This stage can be carried out either by sublimation of the compound (IX) or by heating in the presence of acetic anhydride, at the conclusion of which stage the desired perdeuterated dianhydride monomers are obtained.

Alternatively, the process for the preparation of a monomer of formula (V) can consist in subjecting a compound of formula (X):

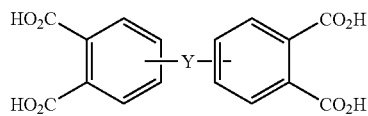

(X)

to deuteration of the aromatic rings at a supercritical pressure, so as to obtain the abovementioned compound of formula (V).

It is specified that the supercritical pressure corresponds to a pressure substantially equal to 220 bar. The compounds of formula (X) may be available commercially from Interchim or can be prepared by conventional methods of synthesis within the scope of a person skilled in the art. The deuteration stage is similar to that already described above.

The invention also relates to a process for the preparation of monomers of formula (VI):

in which $A^1$ and Z correspond to the same definitions as those given above, said process successively comprising the following stages:

reacting a compound of following formula (XI):

with an inorganic acid HX, so as to obtain an ammonium salt of following formula (XII):

in which X represents a halide, such as a chloride or a bromide;

reacting said ammonium salt with deuterated water under an appropriate pressure, followed by reacting with a base, so as to obtain the monomer of formula (VI).

Alternatively, the process for the preparation of a monomer of formula (VI) can consist in reacting the compound of following formula (XI):

with deuterated water in a basic medium under an appropriate pressure, in order to obtain a monomer of formula (VI).

The base compounds of formula (XI) are compounds available commercially from Aldrich and Interchim. The preparation of an ammonium salt consists in reacting an acid, such as hydrochloric acid, with the diamine compound of formula (XI). The ammonium salt formed is subsequently subjected to a deuteration stage which consists in exchanging the hydrogens carried by the aromatic group or groups and the amine groups with deuterium by the action of the deuterated water, followed by a final stage of treatment with a base, such as NaOH or NaOD, in order to obtain the desired deuterated diamine monomers. Preferably, the deuteration stage is carried out at a temperature ranging from 100 to 375° C. under a moderate pressure, for example from 15 to 50 bar, indeed even up to 220 bar, preferably, in a Parr apparatus.

The invention relates to a film (or membrane) based on a deuterated polyimide as defined above.

It is specified that, according to the invention, the term "film" (or "membrane") is understood to mean a uniform layer of polyimide on a support, this layer resulting from the deposition on said support of a poly(amide-acid) solution defined above, said solution having been subjected to a complete imidization treatment. It is specified that this layer may be maintained on the support ("supported film") or may be detached from this same support ("self-supported film").

This film can be prepared by any type of process known to a person skilled in the art.

In particular, these films can be prepared by the hand-coating technique. This technique consists in depositing a poly(amide-acid) solution as defined above on a support, it being possible for the support to be made of a material such as glass. The solution is subsequently dried, for example at a temperature of 65 to 80° C., and then subjected to a heating program, for example at a temperature of 100 to 400° C., in order to imidize the poly(amide-acid) to polyimide. The support can subsequently be immersed in water, allowing the perdeuterated film to become detached.

The film can be characterized by infrared spectroscopy, infrared spectroscopy making it possible in particular to detect the presence of the imide group by an absorption band situated at 1790 cm$^{-1}$ and the bands relating to the C-D bonds appearing within the region between 2000 and 2500 cm$^{-1}$.

These films exhibit excellent mechanical properties, excellent resistance to heat, and transparency within the region from 2500 to 3500 cm$^{-1}$.

Finally, the present invention relates to the use of a deuterated polyimide in accordance with the invention as material which is transparent within the region from 2500 to 3500 cm$^{-1}$.

The invention will now be described with reference to the following examples, given by way of illustration and without limitation.

DETAILED ACCOUNT OF SPECIFIC EMBODIMENTS

Examples 1 to 11 illustrate the preparation of polyimides in accordance with the invention.

Each of these examples illustrates the preparation of a poly(amide-acid) intermediate, followed by the conversion of this intermediate to polyimide.

Each of the polyimides prepared in these examples was characterized by mechanical tests, thermal tests and infrared spectroscopy.

More specifically, the polyimides prepared were characterized mechanically by tensile testing on standardized test specimens cut out with a hollow punch, so as to determine:
the Young's modulus E, expressed in GPa;
the tensile strength, expressed in MPa;
the elongation at break, expressed in %.

The thermal tests consisted in determining the thermal expansion coefficient (written as TEC and expressed in $10^{-5}$ K), it being possible for this coefficient to be determined in two different ways:
either via a polyimide deposited in the form of a film on a support (subsequently entitled "supported method");
or via a polyimide in the form of an unsupported film (subsequently entitled "unsupported method").

Finally, the polyimides prepared were characterized by IR spectroscopy, so as to demonstrate the complete transparency of these polyimides within the region extending from 2500 to 3500 cm$^{-1}$.

EXAMPLE 1

This example illustrates the preparation of a polyimide comprising a backbone formed of an alternation between a repeat unit of formula (Ia) and a repeat unit of formula (IIb):

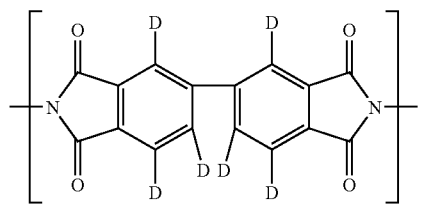
(Ia)

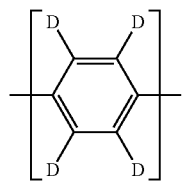
(IIb)

The base reactants are as follows:
$d_6$-3,3',4,4'-biphenyltetracarboxylic dianhydride (abbreviation $d_6$-BPDA) of formula:

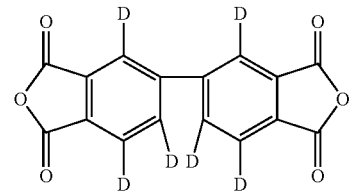

$d_8$-p-phenylenediamine (abbreviation $d_8$-p-PDA) of formula:

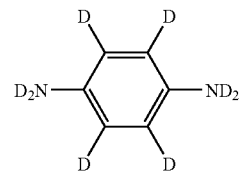

The perdeuterated dianhydride, $d_6$-BPDA, is gradually added to a 250 ml three-necked flask placed under an argon stream comprising the perdeuterated diamine, de-p-PDA, purified beforehand by sublimation and dissolved in anhydrous N-methylpyrrolidone (NMP), in stoichiometric amounts, in order to achieve the desired concentration. The reaction medium is subsequently left stirring at ambient temperature for 20 to 24 hours.

At the end of this stage, the poly(amide-acid) solution obtained, which is light yellow in color and viscous (intrinsic viscosity value of between 230 and 280 ml·g$^{-1}$ with regard to a 5 g·l$^{-1}$ solution at 30° C.), is poured into a specific glass flask.

Subsequently, a film of the poly(amide-acid) solution obtained is deposited on a sheet of glass, said sheet being equipped with shims with a thickness of 20 to 30 μm corresponding to the thickness desired for the film. The sheet of glass is subsequently placed on a thermally regulated plate in order to carry out the drying phase. The heat drying cycle is carried out between 50 and 80° C. with stationary phases. The film obtained after drying is placed in an oven in order to carry out an annealing stage. This stage makes it possible to convert the poly(amide-acid) film to polyimide by a cyclodehydration reaction. The thermal annealing cycle is between 100 and 300° C. with a rate of temperature rise of 1 to 5° C. per minute. The sheet is subsequently immersed in a water bath in order to detach the polyimide film from the sheet of glass.

The $d_6$-BPDA/$d_8$-p-PDA film obtained is subjected to the following analyses;
a transmission IR spectrum;
mechanical tests resulting in Young's modulus, tensile strength and elongation at break values;
a thermal expansion coefficient measurement according to two methods: the unsupported method and the supported method.

The results relating to the abovementioned analyses are combined in table 1 below.

TABLE 1

| Product of example 1 $d_6$-BPDA/$d_8$-p-PDA | Value |
|---|---|
| Young's modulus E (in GPa) | 8 |
| Tensile strength $\sigma_b$ (in MPa) | 335 |
| Elongation at break $\epsilon_b$ (in %) | 20 |
| Thermal expansion coefficient ($10^{-5\circ}$ K) | 0.4–1.7 |
| Vibrational wavelength of the C—D bonds (in cm$^{-1}$) | 2247 |

Thus, the IR spectrum of the product of example 1 exhibits an absorption peak at 2247 cm$^{-1}$, corresponding to the absorption of an aromatic carbon-deuterium bond, and does not exhibit absorption peaks corresponding to the aromatic C—H bonds at 3080 cm$^{-1}$. This product is completely transparent (that is to say, exhibits no optical attenuation) within the region from 2500 to 3500 cm$^{-1}$.

This product also exhibits excellent mechanical properties (tensile strength of 335 MPa) in comparison with products of the prior art.

EXAMPLE 2

This example illustrates the preparation of a polyimide, the backbone of which is formed of an alternation between a repeat unit of formula (Ia) and a repeat unit of formula (IIc):

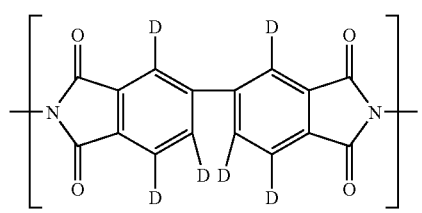
(Ia)

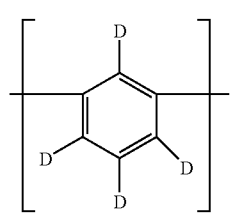
(IIc)

The base reactants are as follows:
$d_6$-3,3',4,4'-biphenyltetracarboxylic dianhydride (abbreviation $d_6$-BPDA) of formula:

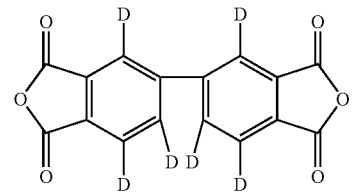

$d_8$-m-phenylenediamine (abbreviation $d_8$-m-PDA) of formula:

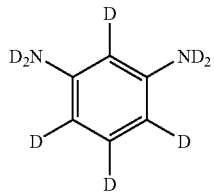

The polyimide described above, entitled $d_6$BPDA/$d_8$-m-PDA, is prepared according to the same procedure as that of example 1 and is subjected to the same analyses.

The results relating to the abovementioned analyses are combined in table 2 below.

TABLE 2

| Product of example 2 $d_6$-BPDA/$d_8$-m-PDA | Value |
|---|---|
| Young's modulus E (in GPa) | 8 |
| Tensile strength $\sigma_b$ (in MPa) | 340 |
| Elongation at break $\epsilon_r$ (in %) | 20 |
| Thermal expansion coefficient ($10^{-5\circ}$ K) | 0.1–1.9 |
| Vibrational wavelength of the C—D bonds (in cm$^{-1}$) | 2255 |

This product is transparent within the region from 2500 to 3500 cm$^{-1}$.

This product also exhibits excellent mechanical properties (such as a tensile strength of 340 MPa) in comparison with products of the prior art.

EXAMPLE 3

This example illustrates the preparation of a polyimide, the backbone of which is formed of an alternation between a repeat unit of formula (Ia) and a repeat unit of formula (IId):

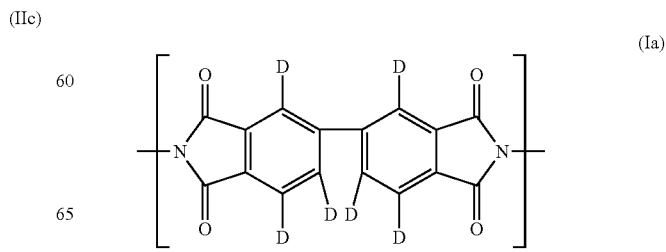
(Ia)

-continued

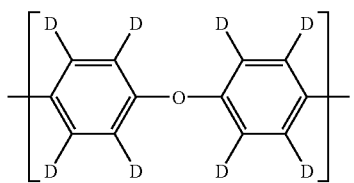
(IId)

The base reactants are as follows:
$d_6$-3,3',4,4'-biphenyltetracarboxylic dianhydride (abbreviation $d_6$-BPDA) of formula:

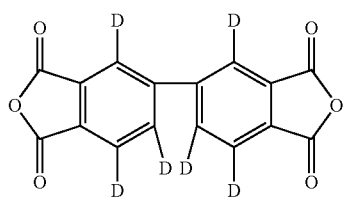

$d_{12}$-oxydianiline (abbreviation $d_{12}$-ODA) of formula:

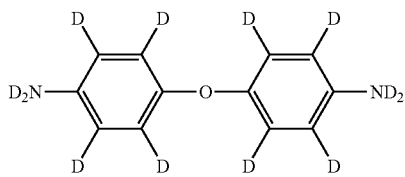

The polyimide described above, entitled $d_6$-BPDA/$d_{12}$-ODA, is prepared according to the same procedure as that of example 1 and is subjected to the same analyses.

The results relating to the abovementioned analyses are combined in table 3 below.

TABLE 3

| Product of example 3 $d_6$-BPDA/$d_{12}$-ODA | Value |
| --- | --- |
| Young's modulus E (in GPa) | 4 |
| Tensile strength $\sigma_b$ (in MPa) | 120 |
| Elongation at break $\epsilon_b$ (in %) | 20 |
| Thermal expansion coefficient ($10^{-5°}$ K) | 1.7–5.0 |
| Vibrational wavelength of C—D bonds (in cm$^{-1}$) | 2254 |

This product is transparent within the region from 2500 to 3500 cm$^{-1}$.

This product also exhibits better mechanical properties (tensile strength of 120 MPa) than the products of the prior art.

EXAMPLE 4

This example illustrates the preparation of a polyimide, the backbone of which is formed of an alternation between a repeat unit of formula (Ib) and a repeat unit of formula (IIb):

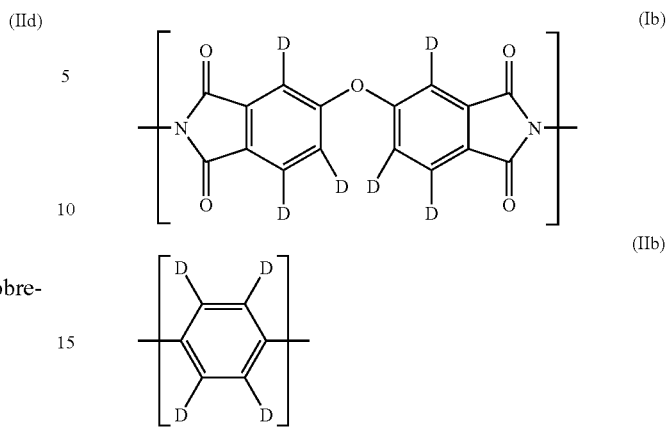

The base reactants are as follows:
$d_6$-bis(3,4-dicarboxyphenyl) ether dianhydride (abbreviation $d_6$-ODPA) of formula:

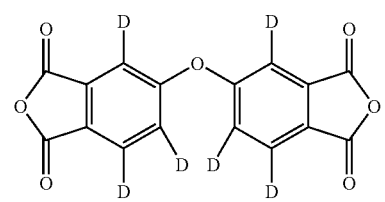

$d_8$-p-phenylenediamine (abbreviation dB-p-PDA) of formula:

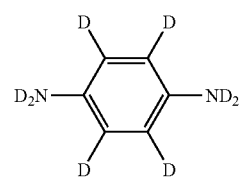

The polyimide described above, entitled $d_6$-ODPA/$d_8$-PDA, is prepared according to the same procedure as that of example 1 and is subjected to the same analyses.

The results relating to the abovementioned analyses are combined in table 4 below.

TABLE 4

| Product of example 4 $d_6$-OPDA/$d_8$-p-PDA | Value |
| --- | --- |
| Young's modulus E (in GPa) | 6 |
| Tensile strength $\sigma_b$ (in MPa) | 180 |
| Elongation at break $\epsilon_b$ (in %) | 15 |
| Thermal expansion coefficient ($10^{-5°}$ K) | 2.6 |
| Vibrational wavelength of the C—D bonds (in cm$^{-1}$) | 2260 |

This product is transparent within the region from 2500 to 3500 cm$^{-1}$.

This product also exhibits very good mechanical properties (tensile strength of 180 MPa) in comparison with products of the prior art.

EXAMPLE 5

This example illustrates the preparation of a polyimide, the backbone of which is formed of an alternation between a repeat unit of formula (Ib) and a repeat unit of formula (IId):

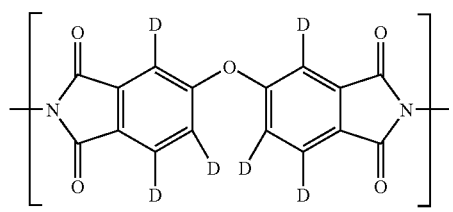
(Ib)

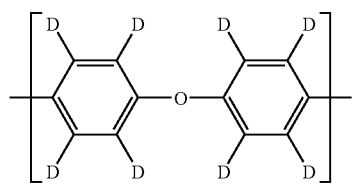
(IId)

The base reactants are as follows:
$d_6$-bis(3,4-dicarboxyphenyl) ether dianhydride (abbreviation $d_6$-ODPA) of formula:

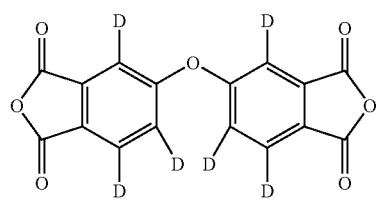

$d_{12}$-oxydianiline (abbreviation $d_{12}$-ODA) of formula:

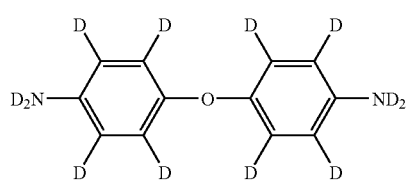

The polyimide described above, entitled $d_6$-ODPA/$d_8$-ODA, is prepared according to the same procedure as that of example 1 and is subjected to the same analyses.

The results relating to the abovementioned analyses are combined in table 5 below.

TABLE 5

| Product of example 5 $d_6$-ODPA/$d_8$-ODA | Value |
|---|---|
| Young's modulus E (in GPa) | 3 |
| Tensile strength $\sigma_b$ (in MPa) | 140 |
| Elongation at break $\epsilon_b$ (in %) | 70 |
| Thermal expansion coefficient ($10^{-5\circ}$ K) | 4 |
| Vibrational wavelength of the C—D bonds (in cm$^{-1}$) | 2255 |

This product is transparent within the region from 2500 to 3500 cm$^{-1}$.

This product also exhibits better mechanical properties (tensile strength of 140 MPa) than the products of the prior art.

EXAMPLE 6

This example illustrates the preparation of a polyimide, the backbone of which is formed of an alternation between a repeat unit of formula (Ic) and a repeat unit of formula (IIb):

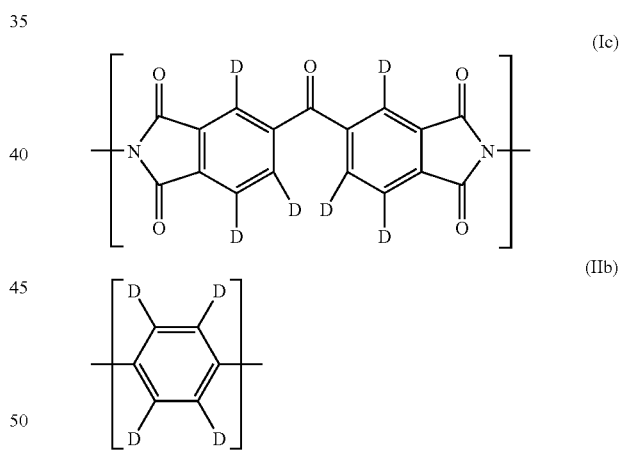
(Ic)

(IIb)

The base reactants are as follows:
$d_6$-3,3',4,4'-benzophenone dianhydride (abbreviation $d_6$-BTDA) of formula:

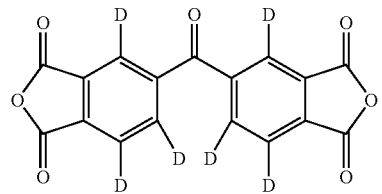

$d_8$-p-phenylenediamine (abbreviation $d_8$-p-PDA) of formula:

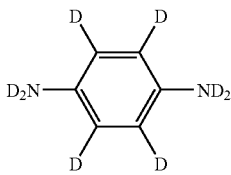

The polyimide described above, entitled $d_6$-BTDA/$d_8$-p-PDA, is prepared according to the same procedure as that of example 1 and is subjected to the same analyses.

The results relating to the abovementioned analyses are combined in table 6 below.

TABLE 6

| Product of example 6 $d_6$-BTDA/$d_8$-p-PDA | Value |
| --- | --- |
| Young's modulus E (in GPa) | 7 |
| Tensile strength $\sigma_b$ (in MPa) | 175 |
| Elongation at break $\epsilon_b$ (in %) | 10 |
| Thermal expansion coefficient ($10^{-5}$° K) | 1.7–4 |
| Vibrational wavelength of the C—D bonds (in cm$^{-1}$) | 2251 |

This product is transparent within the region from 2500 to 3500 cm$^{-1}$.

This product also exhibits very good mechanical properties (tensile strength of 175 MPa) in comparison with products of the prior art.

EXAMPLE 7

This example illustrates the preparation of a polyimide, the backbone of which is formed of an alternation between a repeat unit of formula (Ic) and a repeat unit of formula (IId):

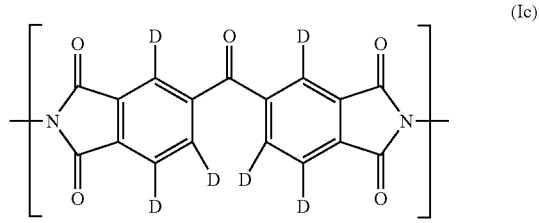
(Ic)

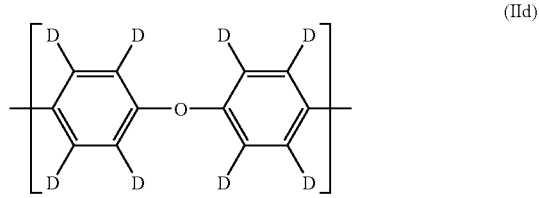
(IId)

The base reactants are as follows:
$d_6$-3,3', 4,4'-benzophenone dianhydride (abbreviation $d_6$-BTDA) of formula:

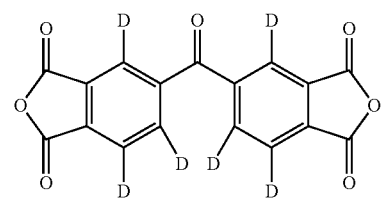

$d_{12}$-oxydianiline (abbreviation $d_{12}$-ODA) of formula:

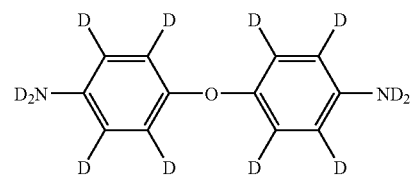

The polyimide described above, entitled $d_6$-BTDA/$d_{12}$-ODA, is prepared according to the same procedure as that of example 1 and is subjected to the same analyses.

The results relating to the abovementioned analyses are combined in table 7 below.

TABLE 7

| Product of example 7 $d_6$-BTDA/$d_{12}$-ODA | Value |
| --- | --- |
| Young's modulus E (in GPa) | 3 |
| Tensile strength $\sigma_b$ (in MPa) | 135 |
| Elongation at break $\epsilon_b$ (in %) | 60 |
| Thermal expansion coefficient ($10^{-5}$° K) | 3.5–5 |
| Vibrational wavelength of the C—D bonds (in cm$^{-1}$) | 2256 |

This product is transparent within the region from 2500 to 3500 cm$^{-1}$.

This product also exhibits better mechanical properties than products of the prior art.

EXAMPLE 8

This example illustrates the preparation of a polyimide, the backbone of which is formed of an alternation between a repeat unit of formula (Id) and a repeat unit of formula (IId):

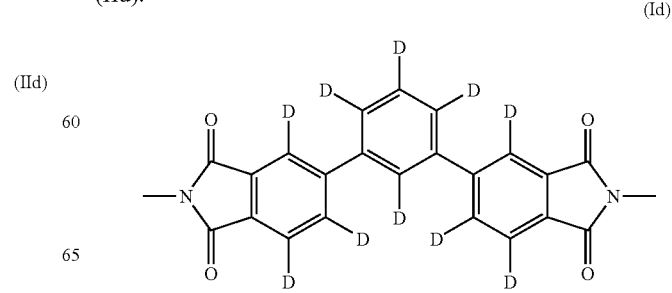
(Id)

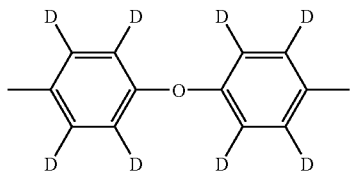 (IId)

The base reactants are as follows:

$d_{10}$-3, 3'',4, 4''-m-terphenyl dianhydride (abbreviation $d_{10}$-MTPDA) of formula:

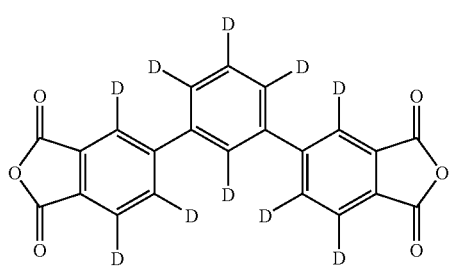

$d_{12}$-oxydianiline (abbreviation $d_{12}$-ODA) of formula:

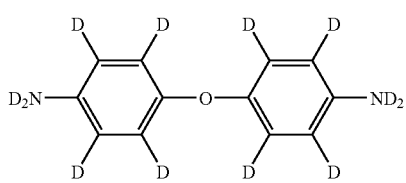

The polyimide described above, entitled $d_{10}$-MTPDA/$d_8$-ODA, is prepared according to the same procedure as that of example 1 and is subjected to the same analyses.

The results relating to the abovementioned analyses are combined in table 8 below.

TABLE 8

| Product of example 8 $d_{10}$-MTPDA/$d_8$-ODA | Value |
|---|---|
| Young's modulus E (in GPa) | 3 |
| Tensile strength $\sigma_b$ (in MPa) | 130 |
| Elongation at break $\epsilon_b$ (in %) | 40 |
| Thermal expansion coefficient ($10^{-5°}$ K) | 2–4 |
| Vibrational wavelength of the C—D bonds (in cm$^{-1}$) | 2240 |

This product is transparent within the region from 2500 to 3500 cm$^{-1}$.

This product also exhibits better mechanical properties (tensile strength of 130 MPa) than products of the prior art.

EXAMPLE 9

This example illustrates the preparation of a polyimide comprising a repeat unit of formula (Ia), a repeat unit of formula (IIb) and a repeat unit of formula (III):

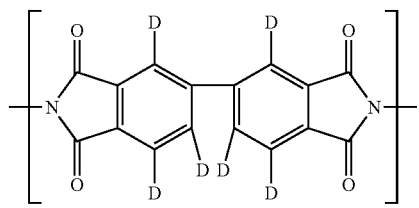 (Ia)

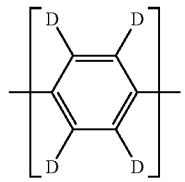 (IIb)

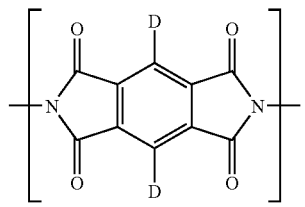 (III)

The base reactants are as follows:

$d_6$-3,3',4,4'-biphenyltetracarboxylic dianhydride (abbreviation $d_6$-BPDA) of formula:

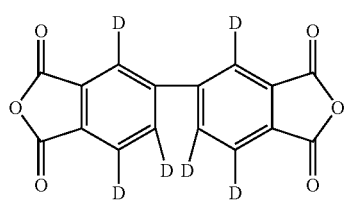

$d_8$-p-phenylenediamine (abbreviation $d_8$-p-PDA) of formula:

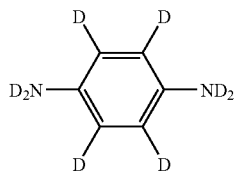

$d_2$-deuterated pyromellitic dianhydride ($d_2$-PMDA) of formula:

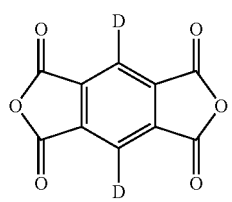

The polyimide described above, entitled $d_6$-BPDA-$d_2$-PMDA-$d_8$-p-PDA, is prepared according to the same procedure as that of example 1 and is subjected to the same analyses.

The results relating to the abovementioned analyses are combined in table 9 below.

TABLE 9

| Product of example 9 $d_6$-BPDA-$d_2$-PMDA-$d_8$-p-PDA | Value |
| --- | --- |
| Young's modulus E (in GPa) | 8 |
| Tensile strength $\sigma_b$ (in MPa) | 300 |
| Elongation at break $\epsilon_b$ (in %) | 25 |
| Thermal expansion coefficient ($10^{-5\circ}$ K) | 1.3 |
| Vibrational wavelength of the C—D bonds (in cm$^{-1}$) | 2257 |

This product is transparent within the region from 2500 to 3500 cm$^{-1}$.

This product also exhibits excellent mechanical properties (tensile strength of 300 MPa) in comparison with products of the prior art.

EXAMPLE 10

This example illustrates the preparation of a polyimide comprising a repeat unit of formula (Ia), a repeat unit of formula (IIb) and a repeat unit of formula (IId):

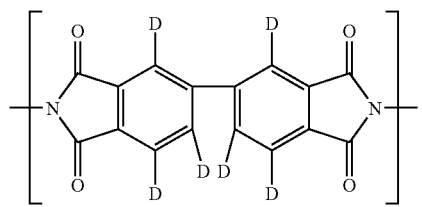
(Ia)

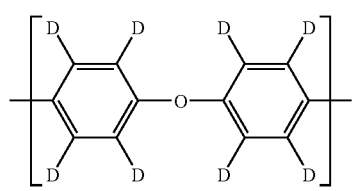
(IId)

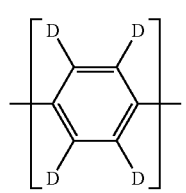
(IIb)

The base reactants are as follows:

$d_6$-3,3',4,4'-biphenyltetracarboxylic dianhydride (abbreviation $d_6$-BPDA) of formula:

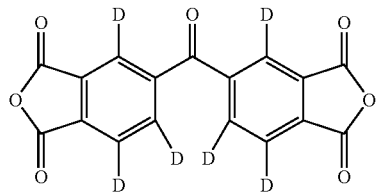

$d_8$-p-phenylenediamine (abbreviation $d_8$-p-PDA) of formula:

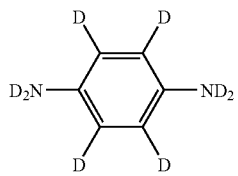

$d_{12}$-oxydianiline (abbreviation $d_{12}$-ODA) of formula:

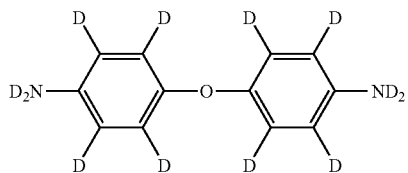

The polyimide described above, entitled $d_6$-BPDA-$d_8$-p-PDA-$d_{12}$-ODA, is prepared according to the same procedure as that of example 1 and is subjected to the same analyses.

The results relating to the abovementioned analyses are combined in table 10 below.

TABLE 10

| Product of example 10 $d_6$-BPDA-$d_8$-p-PDA-$d_{12}$-ODA | Value |
| --- | --- |
| Young's modulus E (in GPa) | 7 |
| Tensile strength $\sigma_b$ (in MPa) | 210 |
| Elongation at break $\epsilon_b$ (in %) | 35 |
| Thermal expansion coefficient ($10^{-5\circ}$ K) | 0.5 |
| Vibrational wavelength of the C—D bonds (in cm$^{-1}$) | 2255 |

This product is transparent within the region from 2500 to 3500 cm$^{-1}$.

This product also exhibits very good mechanical properties (tensile strength of 210 MPa) in comparison with products of the prior art.

EXAMPLE 11

This example illustrates the preparation of a polyimide comprising a repeat unit of formula (Ic), a repeat unit of formula (IIb) and a repeat unit of formula (IId):

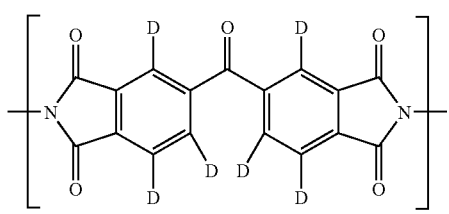
(Ic)

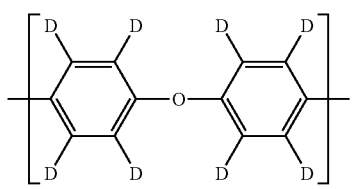
(IId)

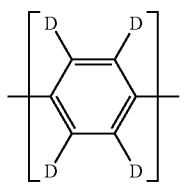
(IIb)

The base reactants are as follows:

$d_6$-3,3',4,4'-benzophenone dianhydride (abbreviation $d_6$-BTDA) of formula:

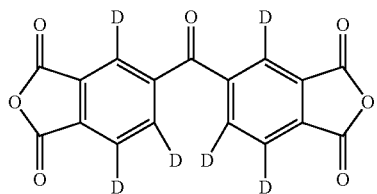

$d_8$-p-phenylenediamine (abbreviation $d_8$-p-PDA) of formula:

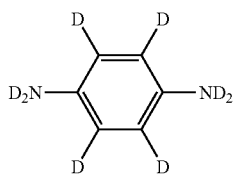

$d_{12}$-oxydianiline (abbreviation $d_{12}$-ODA) of formula:

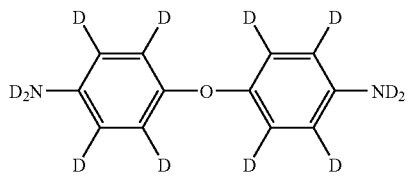

The polyimide described above, entitled $d_2$-BTDA-$d_8$-p-PDA-$d_{12}$-ODA, is prepared according to the same procedure as that of example 1 and is subjected to the same analyses.

The results relating to the abovementioned analyses are combined in table 11 below.

TABLE 11

| Product of example 11 $d_2$-BTDA-$d_8$-p-PDA-$d_{12}$-ODA | Value |
| --- | --- |
| Young's modulus E (in GPa) | 5 |
| Tensile strength $\sigma_b$ (in MPa) | 145 |
| Elongation at break $\epsilon_b$ (in %) | 25 |
| Thermal expansion coefficient ($10^{-5\circ}$ K) | 2 |
| Vibrational wavelength of the C—D bonds (in cm$^{-1}$) | 2262 |

This product is transparent within the region from 2500 to 3500 cm$^{-1}$.

This product also exhibits better mechanical properties than products of the prior art.

REFERENCES CITED

[1] Kaino, Reports on Progress in Polymer Physics in Japan, vol. 43, 2000;
[2] Saint-Clair et al., Sampe Journal, August 1985, pp. 28–33;
[3] U.S. Pat. No. 5,233,018;
[4] U.S. Pat. No. 6,048,986;
[5] Wallace et al., Nuclear Instruments and Methods in Physics Research B 103 (1995), 435–439;
[6] Werstiuk et al., Can. J. Chem., vol. 52, 2169–2171, 1973;
[7] Artamkina et al., translated from Zhurnal Organicheskoi Khimii, vol. 16, No. 4, 99.698–702, April 1980.

The invention claimed is:
1. A deuterated polyimide, the backbone of which comprises an alternation between:
at least one repeat unit corresponding to the following formula (I):

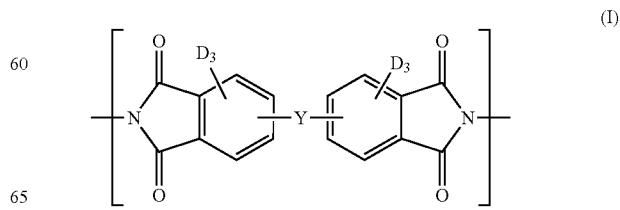
(I)

in which:
Y represents a single bond, —O—, or —CO—; and
at least one repeat unit corresponding to the following formula (II):

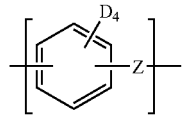

in which:
A¹ represents a perdeuterated aromatic group comprising from 6 to 10 carbon atoms; and
Z represents a single bond or a group chosen from —O—C₆D₄—, —CO—C₆D₄— and —C₆D₄—.

2. The deuterated polyimide as claimed in claim 1, in which the repeat unit in accordance with the formula (II) is a repeat unit of following formula (IIa):

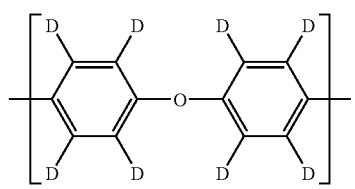

in which Z corresponds to the same definition as that given in claim 1.

3. The deuterated polyimide as claimed in claim 1, chosen from the group consisting of the polyimides chosen from:
polyimides comprising a repeat unit of following formula (Ia) and a repeat unit of following formula (IIb):

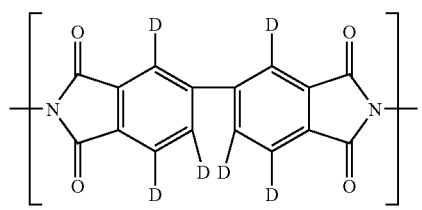

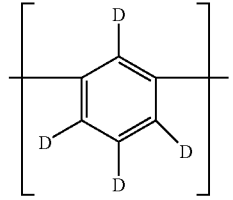

polyimides comprising a repeat unit of following formula (Ia) and a repeat unit of following formula (IIc):

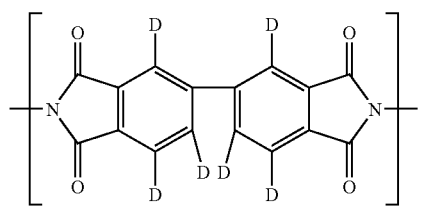

polyimides comprising a repeat unit of following formula (Ia) and a repeat unit of following formula (IId):

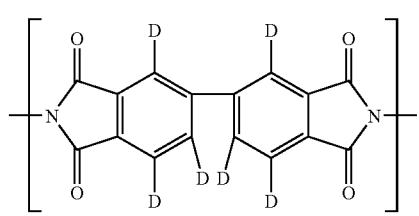

polyimides comprising a repeat unit of following formula (Ib) and a repeat unit of following formula (IIb):

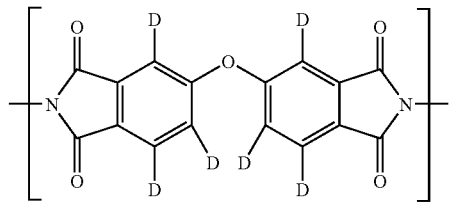

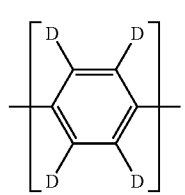

polyimides comprising a repeat unit of following formula (Ib) and a repeat unit of following formula (IId):

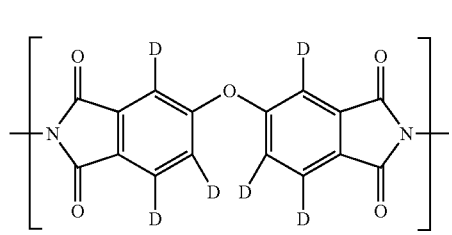
(Ib)

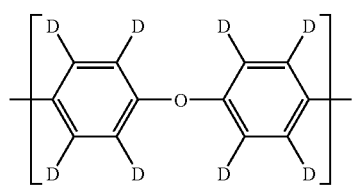
(IId)

polyimides comprising a repeat unit of following formula (Ic) and a repeat unit of following formula (IIb):

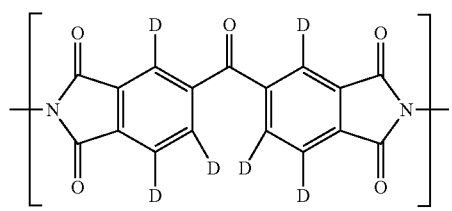
(Ic)

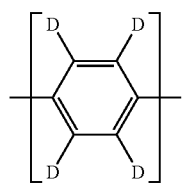
(IIb)

polyimides comprising a repeat unit of following formula (Ic) and a repeat unit of following formula (IId):

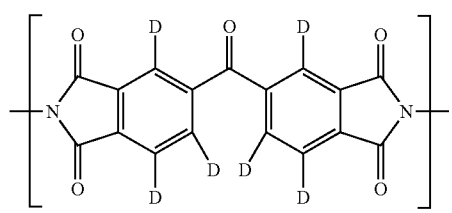
(Ic)

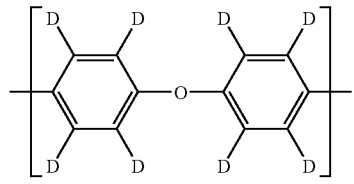
(IId)

polyimides comprising a repeat unit of following formula (Ia), a repeat unit of following formula (IIb) and a repeat unit of following formula (IId):

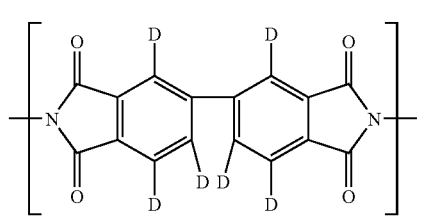
(Ia)

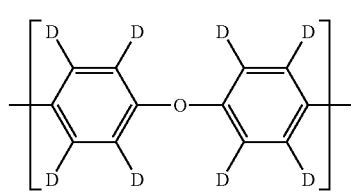
(IId)

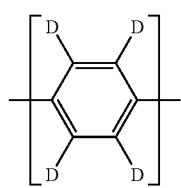
(IIb)

polyimides comprising a repeat unit of following formula (Ic), a repeat unit of following formula (IIb) and a repeat unit of following formula (IId):

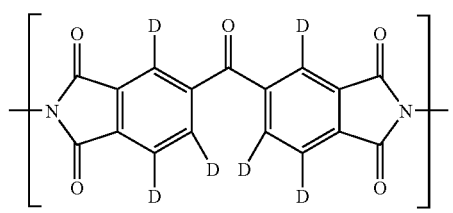
(Ic)

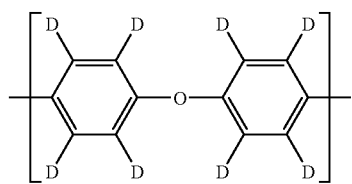
(IId)

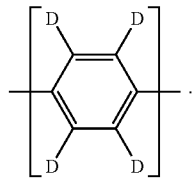
(IIb)

4. The deuterated polyimide as claimed in claim 1, additionally comprising a unit corresponding to the following formula (III):

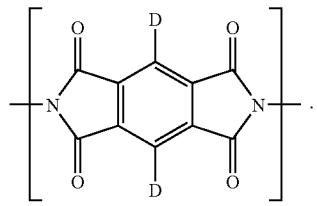
(III)

5. The deuterated polyimide as claimed in claim 4, comprising a repeat unit of following formula (Ia), a repeat unit of following formula (IIb) and a repeat unit of following formula (III):

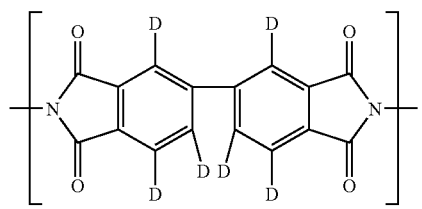
(Ia)

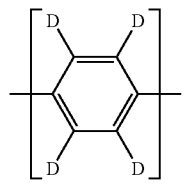
(IIb)

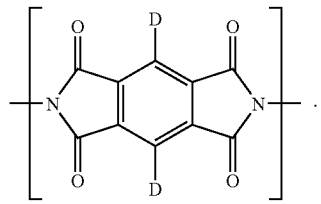
(III)

6. A process for the preparation of a deuterated polyimide, the an alternation between:
at least one repeat unit corresponding to the following formula (I):

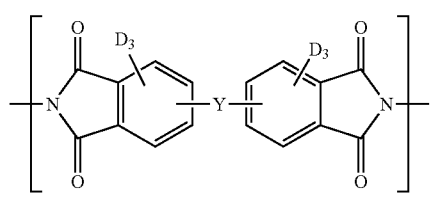
(I)

in which:
—Y represents a single bond, —O—, or —CO—; and
at least one repeat unit corresponding to the following formula (II):

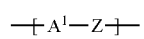
(II)

in which:
$A^1$ represents a perdeuterated aromatic group comprising from 6 to 10 carbon atoms; and
Z represents a single bond or a group chosen from —O—$C_6D_4$—, —CO—$C_6D_4$— and —$C_6D_4$—; said process comprising a stage consisting in treating, by heating at an appropriate temperature, a solution of a poly(amide-acid), the backbone of which comprises an alternation between at least one repeat unit of following formula (IV):

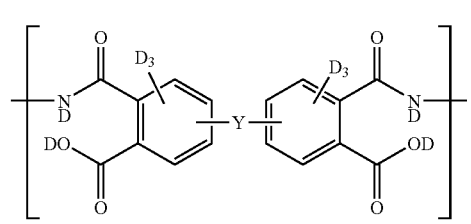
(IV)

in which Y corresponds to the same definition as that given above; and at least one repeat unit of formula (II):

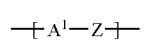
(II)

in which $A^1$ and Z correspond to the same definitions as those given above, the appropriate heating temperature being determined so as to obtain complete imidization of said poly(amide-acid).

7. The preparation process as claimed in claim 6, in which the appropriate heating temperature is a temperature ranging from 80 to 400° C.

8. The preparation process as claimed in claim 6, in which the poly(amide-acid) solution is prepared by polycondensation, in a solvent, of at least one monomer of following formula (V):

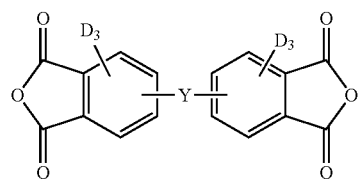
(V)

in which Y corresponds to the same definition as that given in claim 6, and of at least one monomer of following formula (VI):

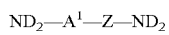   (VI)

in which $A^1$ and Z correspond to the same definitions as those given in claim 6.

9. The preparation process as claimed in claim 6, in which the solvent is a dipolar aprotic solvent chosen from the group consisting of N-methylpyrrolidone (NMP), dimethylformamide (DMF) and dimethylacetamide (DMAC).

10. A film based on a deuterated polyimide, the backbone of which comprises an alternation between:
  at least one repeat unit corresponding to the following formula (I):

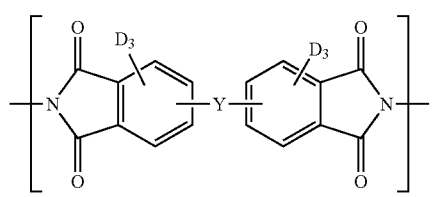   (I)

in which:
  Y represents a single bond, —O—, or —CO—; and
  at least one repeat unit corresponding to the following formula (II):

(II)
—⁅—$A^1$—Z—⁆— in which:
  $A^1$ represents a perdeuterated aromatic group comprising from 6 to 10 carbon atoms; and
  Z represents a single bond or a group chosen from —O—$C_6D_4$—, —CO—$C_6D_4$— and —$C_6D_4$—.

11. The deuterated polyimide as claimed in claim 1, in which the repeat unit in accordance with the formula (II) is a repeat unit of following formula (IIa):

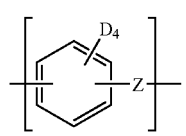   (IIa)

in which Z corresponds to the same definition as that given in claim 1.

12. The deuterated polyimide as claimed in claim 1, chosen from the group consisting of the polyimides chosen from:
  polyimides comprising a repeat unit of following formula (Ia) and a repeat unit of following formula (IIb):

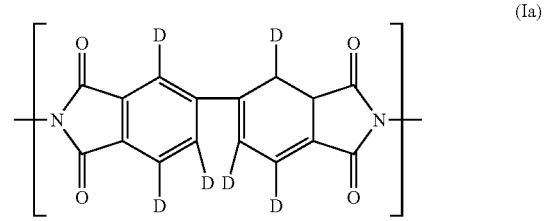   (Ia)

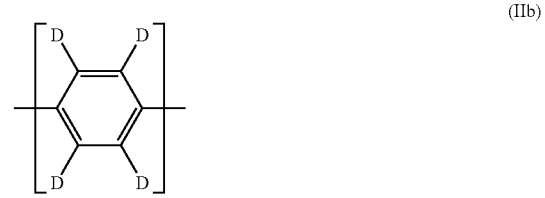   (IIb)

polyimides comprising a repeat unit of following formula (Ia) and a repeat unit of following formula (IIc):

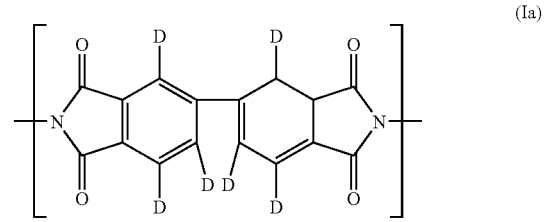   (Ia)

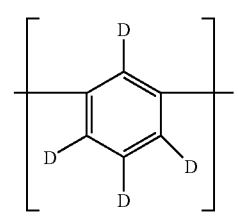   (IIc)

polyimides comprising a repeat unit of following formula (Ia) and a repeat unit of following formula (IId):

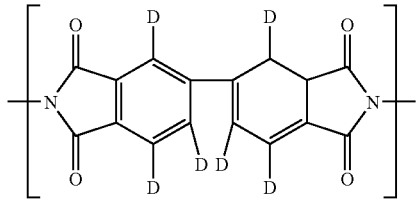
(Ia)

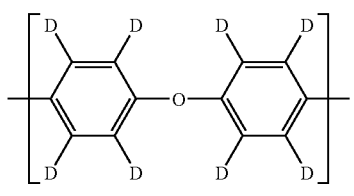
(IId)

polyimides comprising a repeat unit of following formula (Ib) and a repeat unit of following formula (IIb):

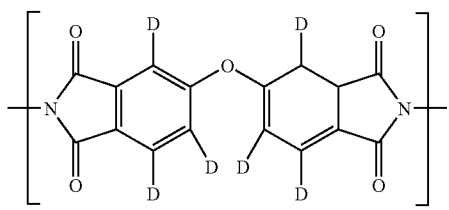
(Ib)

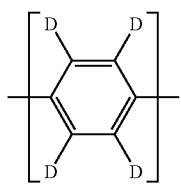
(IIb)

polyimides comprising a repeat unit of following formula (Ib) and a repeat unit of following formula (IId):

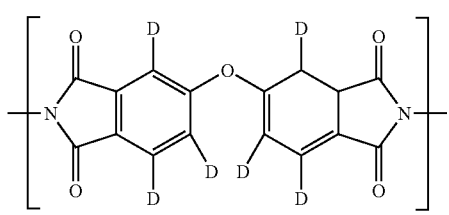
(Ib)

-continued

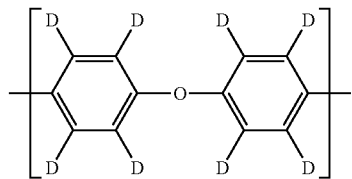
(IId)

polyimides comprising a repeat unit of following formula (Ic) and a repeat unit of following formula (IIb):

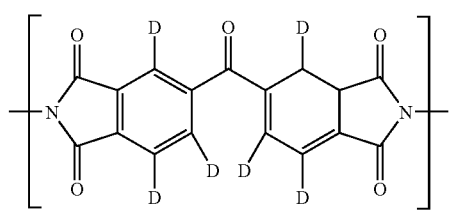
(Ic)

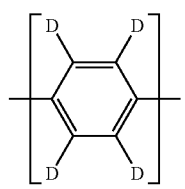
(IIb)

polyimides comprising a repeat unit of following formula (Ic) and a repeat unit of following formula (IId):

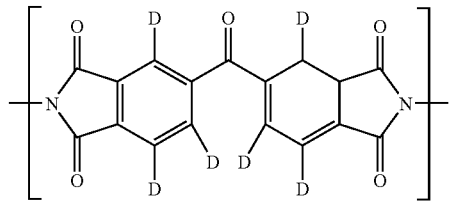
(Ic)

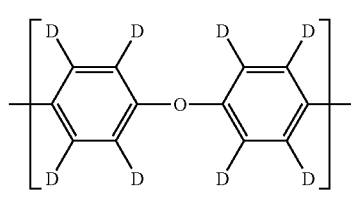
(IId)

polyimides comprising a repeat unit of following formula (Ia), a repeat unit of following formula (IIb) and a repeat unit of following formula (IId):
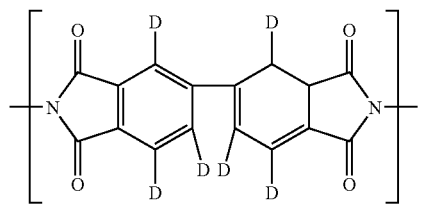
(Ia)
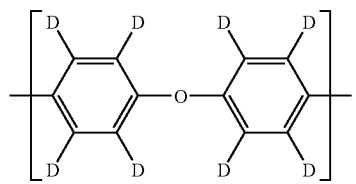
(IId)
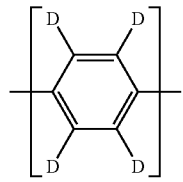
(IIb)
polyimides comprising a repeat unit of following formula (Ic), a repeat unit of following formula (IIb) and a repeat unit of following formula (IId):
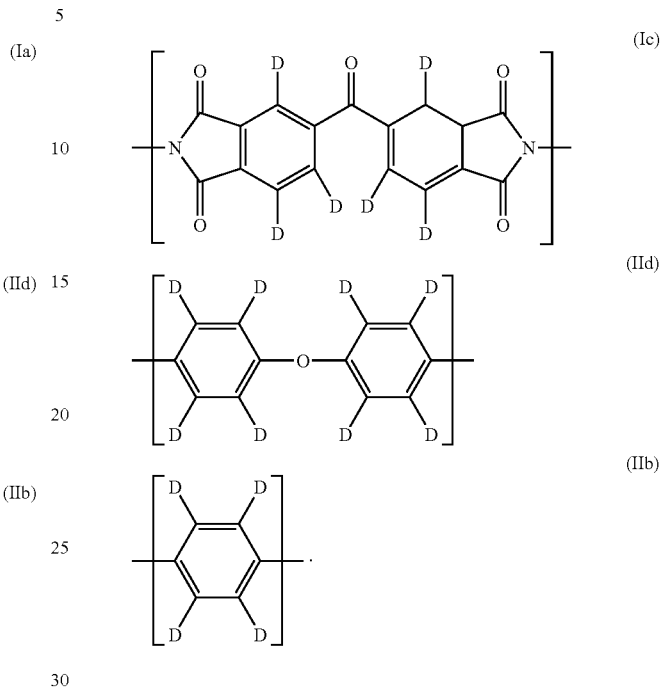
* * * * *

UNITED STATES PATENT AND TRADEMARK OFFICE
CERTIFICATE OF CORRECTION

| | | |
|---|---|---|
| PATENT NO. | : 7,211,632 B2 | Page 1 of 1 |
| APPLICATION NO. | : 10/527630 | |
| DATED | : May 1, 2007 | |
| INVENTOR(S) | : Elsa Anselmi et al. | |

It is certified that error appears in the above-identified patent and that said Letters Patent is hereby corrected as shown below:

On Title Page

IN THE TITLE item 54 and Col. 1, Line 1:

The second word in the title "Polyiimides" should read --Polyimides--.

IN THE CLAIMS:

Column 37, line 53, "the an alternation" should read --the backbone of which comprises an alternation--.

Signed and Sealed this

Fourth Day of September, 2007

JON W. DUDAS
*Director of the United States Patent and Trademark Office*